United States Patent
Xu et al.

(10) Patent No.: US 8,163,529 B2
(45) Date of Patent: *Apr. 24, 2012

(54) NICKING ENDONUCLEASE METHODS AND COMPOSITIONS

(75) Inventors: Shuang-Yong Xu, Lexington, MA (US); Zhenyu Zhu, Beverly, MA (US); Timothy Meixsell, Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/906,515

(22) Filed: Oct. 18, 2010

(65) Prior Publication Data

US 2011/0076720 A1 Mar. 31, 2011

Related U.S. Application Data

(63) Continuation of application No. 11/631,438, filed as application No. PCT/US2005/026249 on Jul. 22, 2005, now Pat. No. 7,820,424.

(60) Provisional application No. 60/590,441, filed on Jul. 22, 2004.

(51) Int. Cl.
| | |
|---|---|
| *C07K 14/00* | (2006.01) |
| *C07H 21/00* | (2006.01) |
| *C12N 9/16* | (2006.01) |
| *C12N 15/00* | (2006.01) |
| *C12N 5/10* | (2006.01) |
| *C12N 1/21* | (2006.01) |
| *C12P 21/00* | (2006.01) |
| *C12Q 1/44* | (2006.01) |

(52) U.S. Cl. .......... 435/196; 435/69.1; 435/320.1; 435/19; 435/252.3; 435/325; 530/350; 536/23.2

(58) Field of Classification Search .......... 435/196, 435/69.1, 320.1, 19, 252.3, 325; 530/350; 536/23.2
See application file for complete search history.

(56) References Cited

U.S. PATENT DOCUMENTS

| | | | |
|---|---|---|---|
| 6,660,475 B2 | 12/2003 | Jack et al. | |
| 7,081,358 B2 | 7/2006 | Heiter et al. | |
| 7,820,424 B2 | 10/2010 | Xu et al. | |
| 2003/0100094 A1 | 5/2003 | Heiter et al. | |

FOREIGN PATENT DOCUMENTS

| | | |
|---|---|---|
| EP | 1176204 A1 | 1/2002 |
| EP | 1199366 A1 | 4/2002 |
| WO | WO-03/087301 A2 | 10/2003 |

OTHER PUBLICATIONS

Branden et al., Introduction to Protein Structure, Garland Publishing Inc., New York, p. 247, 1991.
Witkowski et al., Biochemistry 38: 11643-11650, 1999.
Seffernick et al., J. Bacteriol. 183(8): 2405-2410, 2001.
Abdurashitov M. A. et al., Mol Biol. (Mosk) 30:1261-1267, (1996).
Besnier C.E. et al., EMBL Rep. 2:782-786 (2001).
Geider K. et al., Advan. Expt. Med. Biol. 179:45-54 (1984).
Heitman, et al., Molecular Microbiology, 33: 1141-1151 (1999).
Hsieh et al., J. Bacteriol. 182:949-955 (2000).
Morgan R.D. et al., Biol. Chem. 381:1123-1125 (2000).
Samuelson, et al., Nucleic Acids Research, 32:3661-3671 (2004).
Sasnauskas G. et al., Proc. Natl. Acad. Sci. USA100:6410-6415 (2003).
Stahl et al., Proc Natl Acad Sci USA 93(12):6175-80 (1996).
Stankevicius K. et al., Nucl. Acids Res. 26:1084-1091 (1998).
Xia, Y. et al., Nucl Acids Res. 16:9477-9487, (1988).
Xu Y. et al., Proc. Natl. Acad. Sci. USA 98:12990-12995 (2001).
Zhang Y.N.M. et al., Virology240:366-375 (1998).
Zhu, et al., J. Mol. Biol., 337: 573-583 (2004).

*Primary Examiner* — Delia Ramirez
(74) *Attorney, Agent, or Firm* — Harriet M. Strimpel

(57) ABSTRACT

A nicking endonuclease is described which has an amino acid sequence with at least 70% identity to SEQ ID NO:6 and comprising a mutation at least one of an arginine or glutamic acid corresponding to position 507 and position 546 respectively in SEQ ID NO:6.

2 Claims, 7 Drawing Sheets

Figure 6-1

BsmI DNA and protein sequences (SEQ ID NOS:5 and 6)

```
      ATGAATGTTTTTAGAATTCATGGTGATAATATATTATTGAGTGTGAGAGAGTTATAGATTTG
   1  ----------+----------+----------+----------+----------+----------+   60
       M  N  V  F  R  I  H  G  D  N  I  I  E  C  E  R  V  I  D  L
      ATATTATCAAAAATCAATCCCCAGAAAGTAAAAAGAGGGTTTATTTCATTATCATGCCCT
  61  ----------+----------+----------+----------+----------+----------+  120
       I  L  S  K  I  N  P  Q  K  V  K  R  G  F  I  S  L  S  C  P
      TTTATAGAAATTATATTCAAAGAGGGTCATGATTATTTTCACTGGCGTTTTGATATGTTT
 121  ----------+----------+----------+----------+----------+----------+  180
       F  I  E  I  I  F  K  E  G  H  D  Y  F  H  W  R  F  D  M  F
      CCTGGATTCAATAAAAATACTAACGACAGATGGAATAGCAATATTTTAGATTTGTTAAGT
 181  ----------+----------+----------+----------+----------+----------+  240
       P  G  F  N  K  N  T  N  D  R  W  N  S  N  I  L  D  L  L  S
      CAAAAAGGAAGTTTTTTGTATGAAACTCCAGATGTAATAATTACCAGTTTAAATAATGGA
 241  ----------+----------+----------+----------+----------+----------+  300
       Q  K  G  S  F  L  Y  E  T  P  D  V  I  I  T  S  L  N  N  G
      AAAGAAGAAATTTTAATGGCGATAGAATTTTGTAGTGCTTTACAAGCAGGTAACCAAGCT
 301  ----------+----------+----------+----------+----------+----------+  360
       K  E  E  I  L  M  A  I  E  F  C  S  A  L  Q  A  G  N  Q  A
      TGGCAAAGAAGTGGGCGAGCATATTCGGTAGGTCGAACAGGGTACCCATATATATACATA
 361  ----------+----------+----------+----------+----------+----------+  420
       W  Q  R  S  G  R  A  Y  S  V  G  R  T  G  Y  P  Y  I  Y  I
      GTAGATTTTGTTAAATACGAGTTGAATAATAGTGATAGATCTAGAAAAAACTTGAGATTC
 421  ----------+----------+----------+----------+----------+----------+  480
       V  D  F  V  K  Y  E  L  N  N  S  D  R  S  R  K  N  L  R  F
      CCAAATCCAGCTATACCATATAGTTACATAAGTCACTCAAAAAACACTGGTAATTTTATT
 481  ----------+----------+----------+----------+----------+----------+  540
       P  N  P  A  I  P  Y  S  Y  I  S  H  S  K  N  T  G  N  F  I
      GTGCAAGCATATTTTAGAGGAGAAGAATATCAGCCAAAGTATGATAAAAAACTTAAATTT
 541  ----------+----------+----------+----------+----------+----------+  600
       V  Q  A  Y  F  R  G  E  E  Y  Q  P  K  Y  D  K  K  L  K  F
      TTTGATGAAACTATATTTGCAGAAGATGACATTGCAGACTATATAATTGCAAAGCTACAG
 601  ----------+----------+----------+----------+----------+----------+  660
       F  D  E  T  I  F  A  E  D  D  I  A  D  Y  I  I  A  K  L  Q
      CATCGCGATACCAGCAATATAGAACAATTATTGATAAACAAAAACTTAAAAATGGTTGAA
 661  ----------+----------+----------+----------+----------+----------+  720
       H  R  D  T  S  N  I  E  Q  L  L  I  N  K  N  L  K  M  V  E
      TTCTTATCAAAAAATACAAAAAATGATAATAACTTCACATATTCAGAATGGGAGAGTATC
 721  ----------+----------+----------+----------+----------+----------+  780
       F  L  S  K  N  T  K  N  D  N  N  F  T  Y  S  E  W  E  S  I
      TACAATGGTACATATAGAATAACAAATTTACCTAGTTTAGGGAGATTTAAATTTAGGAAA
 781  ----------+----------+----------+----------+----------+----------+  840
       Y  N  G  T  Y  R  I  T  N  L  P  S  L  G  R  F  K  F  R  K
      AAGATTGCTGAAAAGTCTCTTTCAGGAAAAGTTAAGGAATTTAACAATATTGTTCAGAGA
 841  ----------+----------+----------+----------+----------+----------+  900
       K  I  A  E  K  S  L  S  G  K  V  K  E  F  N  N  I  V  Q  R
      TATAGTGTAGGTCTTGCTTCAAGTGATTTACCTTTTGGAGTTATAAGAAAAGAATCAAGA
 901  ----------+----------+----------+----------+----------+----------+  960
       Y  S  V  G  L  A  S  S  D  L  P  F  G  V  I  R  K  E  S  R
      AATGATTTTATTAACGATGTATGTAAACTTTATAATATAAATGATATGAAAATAATTAAA
 961  ----------+----------+----------+----------+----------+----------+ 1020
       N  D  F  I  N  D  V  C  K  L  Y  N  I  N  D  M  K  I  I  K
      GAGCTAAAAGAAGATGCGGACCTTATTGTCTGTATGCTTAAGGGATTTAAACCTAGAGGA
1021  ----------+----------+----------+----------+----------+----------+ 1080
       E  L  K  E  D  A  D  L  I  V  C  M  L  K  G  F  K  P  R  G
      GATGATAATCGACCGGATAGAGGAGCGTTACCCCTTGTTGCTATGCTAGCCGGAGAAAAT
1081  ----------+----------+----------+----------+----------+----------+ 1140
       D  D  N  R  P  D  R  G  A  L  P  L  V  A  M  L  A  G  E  N
      GCACAAATTTTTACATTTATTTATGGACCATTAATAAAAGGGGCTATAAATTTGATTGAC
1141  ----------+----------+----------+----------+----------+----------+ 1200
       A  Q  I  F  T  F  I  Y  G  P  L  I  K  G  A  I  N  L  I  D
      CAGGATATCAATAAGCTTGCAAAACGTAACGGGCTTTGGAAATCCTTTGTAAGTTTAAGT
1201  ----------+----------+----------+----------+----------+----------+ 1260
       Q  D  I  N  K  L  A  K  R  N  G  L  W  K  S  F  V  S  L  S
      GACTTTATTGTTTTGGACTGTCCTATTATCGGAGAATCTTATAATGAATTTCGTTTAATC
1261  ----------+----------+----------+----------+----------+----------+ 1320
       D  F  I  V  L  D  C  P  I  I  G  E  S  Y  N  E  F  R  L  I
```

Figure 6-2

```
      ATAAATAAGAACAATAAAGAGTCCATTTTACGCAAAACTAGCAAACAACAAAATATTTTG
1321  ----------+----------+----------+----------+----------+----------+  1380
       I  N  K  N  N  K  E  S  I  L  R  K  T  S  K  Q  Q  N  I  L
      GTTGATCCAACACCTAATCATTATCAAGAAAATGATGTGGATACAGTTATATACTCTATA
1381  ----------+----------+----------+----------+----------+----------+  1440
       V  D  P  T  P  N  H  Y  Q  E  N  D  V  D  T  V  I  Y  S  I
      TTTAAATATATTGTACCTAATTGTTTTAGTGGGATGTGTAATCCACCTGGAGGAGACTGG
1441  ----------+----------+----------+----------+----------+----------+  1500
       F  K  Y  I  V  P  N  C  F  S  G  M  C  N  P  P  G  G  D  W
      AGTGGCCTATCAATAATAAGAAATGGTCATGAATTTAGGTGGTTATCACTTCCTCGAGTT
1501  ----------+----------+----------+----------+----------+----------+  1560
       S  G  L  S  I  I  R  N  G  H  E  F  R  W  L  S  L  P  R  V
      AGTGAGAATGGAAAAAGACCCGACCATGTAATACAAATACTTGATCTTTTTGAAAAACCC
1561  ----------+----------+----------+----------+----------+----------+  1620
       S  E  N  G  K  R  P  D  H  V  I  Q  I  L  D  L  F  E  K  P
      CTTTTATTAAGTATTGAGTCAAAAGAAAAACCTAATGATCTTGAACCAAAAATAGGGGTG
1621  ----------+----------+----------+----------+----------+----------+  1680
       L  L  L  S  I  E  S  K  E  K  P  N  D  L  E  P  K  I  G  V
      CAGTTAATAAAATACATAGAGTATCTATTTGATTTTACTCCTAGTGTTCAAAGAAAGATA
1681  ----------+----------+----------+----------+----------+----------+  1740
       Q  L  I  K  Y  I  E  Y  L  F  D  F  T  P  S  V  Q  R  K  I
      GCCGGGGGAAATTGGGAGTTTGGTAATAAAAGCCTGGTTCCTAACGATTTTATTCTATTG
1741  ----------+----------+----------+----------+----------+----------+  1800
       A  G  G  N  W  E  F  G  N  K  S  L  V  P  N  D  F  I  L  L
      TCTGCAGGTGCATTCATCGATTATGACAATCTTACAGAAAATGATTATGAAAAAATTTTT
1801  ----------+----------+----------+----------+----------+----------+  1860
       S  A  G  A  F  I  D  Y  D  N  L  T  E  N  D  Y  E  K  I  F
      GAAGTCACTGGTTGTGATTTACTGATTGCTATTAAAAACCAGAATAACCCTCAGAAGTGG
1861  ----------+----------+----------+----------+----------+----------+  1920
       E  V  T  G  C  D  L  L  I  A  I  K  N  Q  N  N  P  Q  K  W
      GTGATTAAATTCAAACCTAAAAATACTATAGCAGAGAAATTAGTTAACTATATAAAGCTT
1921  ----------+----------+----------+----------+----------+----------+  1980
       V  I  K  F  K  P  K  N  T  I  A  E  K  L  V  N  Y  I  K  L
      AATTTTAAAAGTAATATATTTGATACAGGATTTTTTCATATAGAGGGATAA
1981  ----------+----------+----------+----------+--------+-  2031
       N  F  K  S  N  I  F  D  T  G  F  F  H  I  E  G  *
```

NICKING ENDONUCLEASE METHODS AND COMPOSITIONS

CROSS REFERENCE

This application is a continuation of U.S. application Ser. No. 11/631,438, filed Jan. 3, 2007, which is a §371 application of international application number PCT/US2005/026249 filed on Jul. 22, 2005, which claims priority from U.S. provisional application No. 60/590,441 filed on Jul. 22, 2004, herein incorporated by reference.

BACKGROUND OF THE INVENTION

There are over 240 Type II restriction endonucleases (REases) with unique specificities discovered so far from bacterial and viral sources. In contrast, only eight site-specific nicking enzymes are commercially available. Nonetheless, nicking endonucleases are believed to be useful in a variety of contexts including strand displacement amplification and DNA cloning (U.S. Pat. No. 6,660,475; Janulaitis et al., EP1176204A1, WO 03/087301)

Certain sequence-specific DNA nicking enzymes have been found to occur naturally. Nt.CviQXI (CviNY2A, R^AG) and Nt.CviPII (CviNYSI, ^CC(A/G/T)) were originally found in the lysates of *Chlorella* viruses (Xia, Y. et al. *Nucl Acids Res.* 16:9477-9487, (1988); Zhang Y. N. M. et al. *Virology* 240:366-375 (1998). The nicking enzymes N.BstSEI and N.BstNBI were identified in bacterial sources (Abdurashitov M. A. et al. *Mol Biol.* (*Mosk*) 30:1261-1267, (1996); Morgan R. D. et al. *Biol. Chem.* 381:1123-1125 (2000)). Bacteriophages also encode nicking enzymes such as the gene II protein of bacteriophage f1 that is essential for viral DNA replication (Geider K. et al. *Advan. Expt. Med. Biol.* 179:45-54 (1984)).

Sequence-specific DNA nicking enzymes have also been created by mutating naturally occurring dimeric Type IIA, Type IIS (Xu Y. et al. *Proc. Natl. Acad. Sci. USA* 98:12990-12995 (2001); Besnier C. E. et al. *EMBL Rep.* 2:782-786 (2001); Zhu Z. et al. *J. Mol. Biol.* 337:573-583 (2004)) or Type IIT restriction endonucleases using a variety of approaches.

Type II restriction endonucleases (REase) generally have two subunits forming either a homodimer or a heterodimer.

For homodimeric EcoRV, Stahl et al. (*Proc Natl Acad Sci USA* 93 (12):6175-80 (1996)) described combining a subunit with an inactive catalytic activity with a second subunit with a deficiency in DNA binding to produce a nicking endonuclease that is non-specific with respect to which strand is nicked.

Heitman (*Mol. Microbiol.* 33:1141-1151 (1999)) created EcoRI nicking endonucleases with R200c, R200K, or E144C mutations.

Xu (*Proc. Natl. Acad. Sci. USA* 98:12990-12995 (2001)) reported the creation of N.AlwI by domain exchange between the Type IIS REase AlwI and a homologous, naturally occurring nicking enzyme, N.BstNBI. This nicking endonuclease predominantly nicks the top DNA strand of a DNA duplex as a monomer. This domain exchange method requires prior knowledge of the dimerization domain and a relatively high amino acid sequence similarity with a naturally existing nicking enzyme.

Site-directed mutagenesis of MlyI REase resulted in variants in which the dimerization function was disrupted. The resulting nicking enzyme is strand-specific, cleaving the top strand of the wild type recognition sequence. However, no bottom strand nicking enzyme was ever isolated from MlyI (Besnier C. E. et al. *EMBL Rep.* 2:782-786 (2001).

The DNA nicking activity of BfiI can be enhanced by alteration of reaction conditions. By lowering the pH value in the cleavage reaction, the BfiI REase can be converted to a bottom-strand specific nicking enzyme (Sasnauskas G. et al. *Proc. Natl. Acad. Sci. USA* 100:6410-6415 (2003)).

Zhu (*J. Mol. Biol.* 337:573-583 (2004)) used random mutagenesis and back-crosses with the Type IIS restriction endonucleases to generate BsaI, BsmAI and BsmBI nicking variants. There was no selectivity in nicking strand specificity. The random mutagenesis method required screening a large number of mutants.

Samuelson (*Nucl. Acids Res.* 32:3661-3671 (2004)) designed a SapI substrate site into the expression plasmid to allow for in vitro selection of plasmid clones from a randomly mutated SapI expression library possessing a site-specific and strand-specific nick. Bottom-strand nicking enzymes yielded Nb.SapI-1 containing a critical R420I substitution near the end of the protein while a separate top-strand selection procedure yielded several SapI variants with a distinct preference for top-strand cleavage.

Nicking endonucleases have been created from heterodimeric Type IIT including Bpu10I (Stankevicius K. et al. *Nucl. Acids Res.* 26:1084-1091 (1998), EP 1176204 A1, July 2000, BbvCI (US patent application 2003/0100094 and BslI (Hsieh et al. *J. Bacteriol.* 182:949-955 (2000)) These nicking endonucleases were formed by inactivation of the catalytic activity of one subunit in the heterodimer.

Nicking BsmAI and BsmB1 have been made by error prone PCR and site directed mutagenesis (U.S. application Ser. No. 11/013,235).

SUMMARY OF THE INVENTION

In an embodiment of the invention, a nicking endonuclease is described that has an amino acid sequence with at least 70% identity to SEQ ID NO:6 and includes a mutation at an arginine corresponding to position 507 in SEQ ID NO:6. The nicking endonuclease may further contain a mutation at a glutamic acid corresponding to position 546 in SEQ ID NO:6. The DNA encoding the nicking endonuclease has at least 90% sequence identity with SEQ ID NO:5.

In an embodiment of the invention a nicking endonuclease is described that has an amino acid sequence with at least 70% identity to SEQ ID NO:6 and includes a mutation at a glutamic acid corresponding to position 546 in SEQ ID NO:6. The DNA encoding the nicking endonuclease has at least 90% sequence identity with SEQ ID NO:5.

In an example of the above, the arginine can be changed to an aspartic acid and the glutamic acid to a valine.

In an embodiment of the invention, a method is provided of forming a nicking endonuclease from a restriction endonuclease having an amino acid sequence. This method includes: mutagenizing at least one of an arginine or a glutamic acid in the amino acid sequence by targeted mutagenesis; cloning the mutagenized restriction endonuclease and assaying the mutant for nicking activity.

The method is exemplified by starting with BsmI restriction endonuclease or an isoschizomer or neoisoschizomer thereof and mutagenizing this enzyme in the manner described above.

BRIEF DESCRIPTION OF THE DRAWINGS

FIG. 6 shows the DNA and protein sequence for BsmI restriction endonuclease. The arginine codons and residues are highlighted in bold font and the glutamic acid codons and residues are highlighted in italics.

DETAILED DESCRIPTIONS OF THE INVENTION

In an embodiment of the invention, strand-specific DNA nicking enzymes are engineered from existing Type IIA/IIS that lack significant double strand cleavage activity. The genetic screen described here employs a site directed mutagenesis approach without prior knowledge of protein structure or active sites. Certain charged amino acids, in particular, arginine and/or glutamic acid are targeted and substituted by neutral or oppositely charged amino acids. This genetic screen is exemplified here for BsmI.

Methylase protected cells are generated by cloning the appropriate methylase gene into a vector for example pACYC184, capable of being replicated in a host bacterial cell such as E. coli. The restriction endonuclease gene of interest is cloned in a second vector, for example, pUC19. The restriction enzyme gene can alternatively be expressed in other vectors with T7 promoter, phage SP6 promoter, $P_{trp}$, $P_{tac}$, $lac_{UV5}$ promoter, $P_L$, $P_R$, or $P_{ara}$ and used as the template for inverse PCR.

Once cloned, the restriction endonuclease gene can be mutated using any method of targeted mutagenesis known in the art. For example, inverse PCR is used in Example 1. It was noted previously that a nicking endonuclease, which was created by random mutagenesis of the BsaI restriction endonuclease gene had mutated arginine residues. Consequently, present embodiments of the invention target arginine residues. Each Arg codon can be identified from the gene sequence and then changed one at a time to a different codon, for example, aspartic acid. The amino acid encoded by the altered codon can be any non-acidic amino acid. The choice of aspartic acid was arbitrary. Individual mutants can be cloned and assayed for nicking activity and desirably an absence of double strand cleavage activity. In addition to arginine residues, other targets of mutation include Asp, Gln, and Lys, which may be mutated to amino acids having a different charge. Once a suitable nicking endonuclease is obtained, the enzyme can be purified and assayed for nicking activity (US 2003-0100094 A1) and strand nicking specificity (Xu et al. 2004 J. Mol Biol. 337:573-583).

Figure 4:
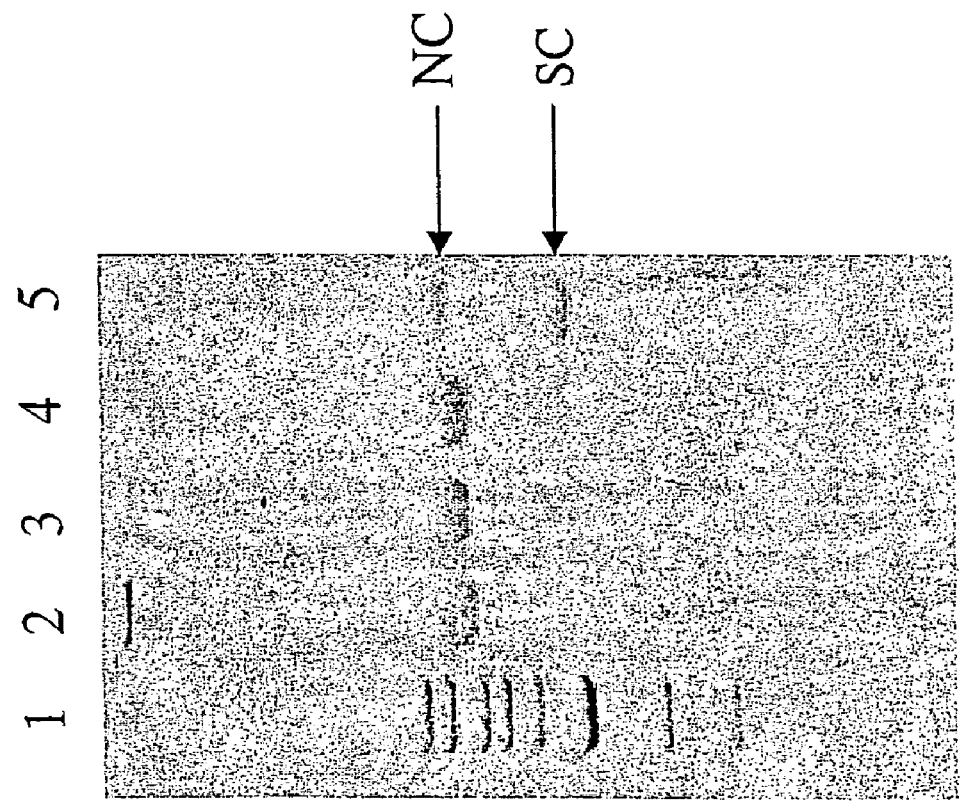
FIG. 4 shows the DNA nicking activity assay for crude Nb.BsmI (E546V). Variant E546V nicking endonuclease was diluted and used for the nicking assay. Lane 1, 1 kb DNA size marker, lane 2, 1× undiluted cell extract; lanes 3, 4, and 5, pBR322 incubated with 10-, $10^2$-, $10^3$-fold diluted cell extracts containing E546V nicking enzyme.

In one embodiment of the invention, bsmIR is mutated to yield a nicking endonuclease. This enzyme has 30 Arg residues although the number of Arg residues varies among different endonucleases. By substituting each arginine for an aspartate in thirty separate clones (see below), one nicking endonuclease (isolate #26) with high level of nicking activity and substantially no double strand cleavage activity was obtained. This mutant was identified as R507D. When the allele of isolate #26 was sequenced, it was found to carry two additional mutations/amino acid substitutions and was characterized as R507D/G509V/E546V. The nicked pBR322DNA was subjected to run-off sequencing to determine the strand specificity. The triple mutant R507D/G509V/E546V nicked the bottom strand of BsmI site with the strand specificity of G^CATTC. An additional nicking endonuclease was prepared which was derived from #26 but contained a single mutated Glutamic acid (E546V). This mutant had some minor double strand cleavage activity of less than 20% (FIG. 4).

Mutations identified as effective for converting a restriction endonuclease into a nicking endonuclease can be introduced into isoschizomers to generate strand specific nicking variants. For example, for BsmI, the R507D and/or E546V substitutions (or R507X, E546X, X=the rest of 19 amino acid residues) can be introduced into BsmI isoschizomers/neoschizomers such as BsaMI, Mva1269I, PctI, Asp26HI, Asp27I, Asp35I, Asp36I, Asp40I, Asp50I, BscCI, Uba1382I, and Uba1415I in the equivalent positions to generate strand-specific nicking variants.

The present embodiments are further illustrated by the following Examples. These Examples are not intended to be limiting.

The references cited above and below as well as provisional application Ser. No. 60/590,441 are hereby incorporated by reference.

EXAMPLES

Example 1

Construction of a High Expression Clone of BsmI Endonuclease by Targeted Mutagenesis (a) Cloning bsmIM into pACYC184

The bsmIM gene was first amplified by PCR and cloned into pACYC184 to construct a protected expression host ER2683 [pACYC-bsmIM]. ER2683 carries the $lacI^q$ gene and therefore Lac repressors are over-produced in this strain.

(b) Cloning bsmIR into pUC19

The bsmIR gene was amplified in PCR using the following primers:

```
                                              (SEQ ID NO: 1)
5'GGTGGTGCATGCGGAGGTAAATAAATGAATGTTTTTAGAATTCA
TGGTGATAAT3'
(303-096, underlined, SphI site)
```

```
                                              (SEQ ID NO: 2)
5'GGTGGTGACGTCTTATCCCTCTATATGAAAAAATCCTGT3'
(303-095, underlined, ZraI site).
```

PCR was conducted as follows: 4 units of Deep Vent DNA polymerase, 2, 4, and 8 mM $MgSO_4$, 1× Thermopol buffer, 0.4 nM dNTP, 1 µg of Bacillus stearothermophilus NUB36 genomic DNA template. 0.24 μg (~0.4 to 0.8 mM) primers 303-095 and 303-096. The PCR DNA was digested with SphI and ZraI and ligated to pUC19 with compatible cohesive ends (SphI/SfoI). Cell extracts from 8 clones displayed BsmI endonuclease activity. The entire bsmIR gene for the #2 clone was sequenced and was found to encode the wild-type sequence (see FIG. 6). This plasmid was named pUC-bsmIR and used for expression and mutagenesis. The expression strain was ER2683 [pACYC-bsmIM, pUC-bsmIR]. The BsmI restriction endonuclease yield was estimated to be at approximately $10^6$ units/gram of wet cells.

Example 2

Mutagenesis Scanning of BsmI Endonuclease to Isolate Nicking Variants

Using inverse PCR, each Arg codon was changed to Asp codon (GAT) with one Arg mutation per clone. A total of 60 PCR primers were synthesized in order to make the 30 site-directed mutants. The primers were about 39 nucleotides in length which provided sequence on either side of the arginine codon (see FIG. 6). For example, in order to mutagenize Arg507 to Asp507 (R507D), the following primers were made:

```
                                   (SEQ ID NO: 3)
5' AGCGGCCTATCAATAATAGATAATGGTCATGGATTTAGG 3'
(309-242, underlined, Asp codon)

(SEQ ID NO: 4)
5'CCTAAATTCATGAACATTATCTATTATTGATAGGCCACT3'
(309-243).
```

The inverse PCR conditions were as follows: 4 units of Deep Vent DNA polymerase, 1× Thermopol buffer, 0.4 nM dNTP, 0.2 μg pUC-BsmIR DNA template, 0.4-0.8 μM primers 309-242 and 309-243, 95° C. for 30 sec, 55° C. for 30 sec, 72° C. for 4 min and 31 sec, 20-25 cycles and either 2, 4, and 8 mM MgSO. Thirty PCR products were purified by Qiagen spin columns, digested with DpnI, and transferred into ER2683 [pACYC-bsmIM] by transformation. Four colonies for each mutant were cultured in 5 ml LB plus Ap and Cm overnight and cell extracts were prepared by sonication. Supercoiled plasmid DNA pBR322 was used as the substrate for the nicking assay. Detection of nicked circular DNA was an indication of nicking activity. The DNA nicking activity or double-stranded DNA (ds-DNA) cleavage activity of the mutants are summarized below:

| | | |
|---|---|---|
| 1. | R5D | ds-DNA cleavage |
| 2. | R16D | ds-DNA cleavage |
| 3. | R32D | ds-DNA cleavage |
| 4. | R56D | ds-DNA cleavage |
| 5. | R70D | ds-DNA cleavage |
| 6. | R123D | low nicking activity |
| 7. | R126D | low nicking activity, low ds-DNA cleavage |
| 8. | R132D | ds-DNA cleavage |
| 9. | R153D | ds-DNA cleavage |
| 10. | R155D | low nicking activity, low ds-DNA cleavage |
| 11. | R159D | low nicking activity |
| 12. | R186D | low nicking activity, low ds-DNA cleavage |
| 13. | R222D | ds-DNA cleavage |
| 14. | R266D | ds-DNA cleavage |
| 15. | R275D | ds-DNA cleavage |
| 16. | R279D | ds-DNA cleavage |
| 17. | R300D | ds-DNA cleavage |
| 18. | R316D | ds-DNA cleavage |
| 19. | R320D | ds-DNA cleavage |
| 20. | R359D | low nicking activity, low ds-DNA cleavage |
| 21. | R364D | low nicking activity |
| 22. | R367D | low nicking activity |
| 23. | R409D | ds-DNA cleavage |
| 24. | R438D | ds-DNA cleavage |
| 25. | R451D | ds-DNA cleavage |
| 26. | R507D | high nicking activity |
| 27. | R513D | ds-DNA cleavage |
| 28. | R519D | low nicking activity, low ds-DNA cleavage |
| 29. | R526D | intermediate nicking activity |
| 30. | R578D | ds-DNA cleavage |

Figure 1:
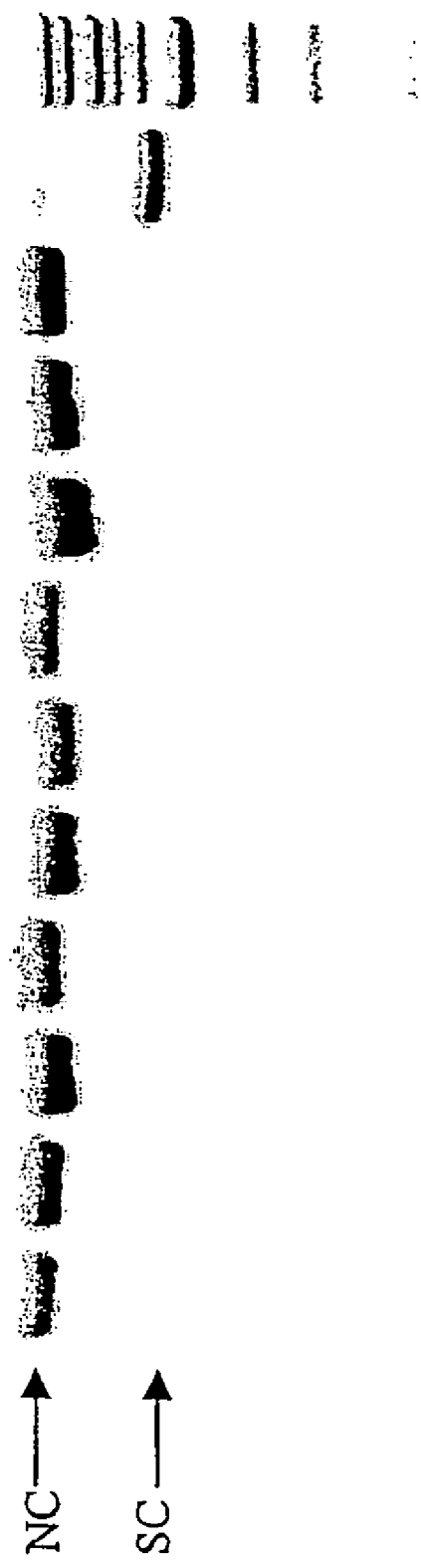
FIG. 1 shows the DNA nicking activity assay for Nb.BsmI (R507D/G509V/E546V) in different reaction buffers. Lanes 1 to 10, pBR322 digested with Nb.BsmI in NEB (New England Biolabs, Inc., Ipswich, Mass.) buffer 1, 2, 3, 4, BamHI buffer, Sau3AI buffer, Thermopol buffer, MwoI buffer, high pH Tris-HCl buffer (pH 8.8), Taq DNA pol buffer, respectively; lane 11, pBR322DNA; lane 12, DNA size marker. Plasmid pBR322 contains one BsmI site. NC, nicked circular DNA. SC, supercoiled circular DNA.
Figure 2:
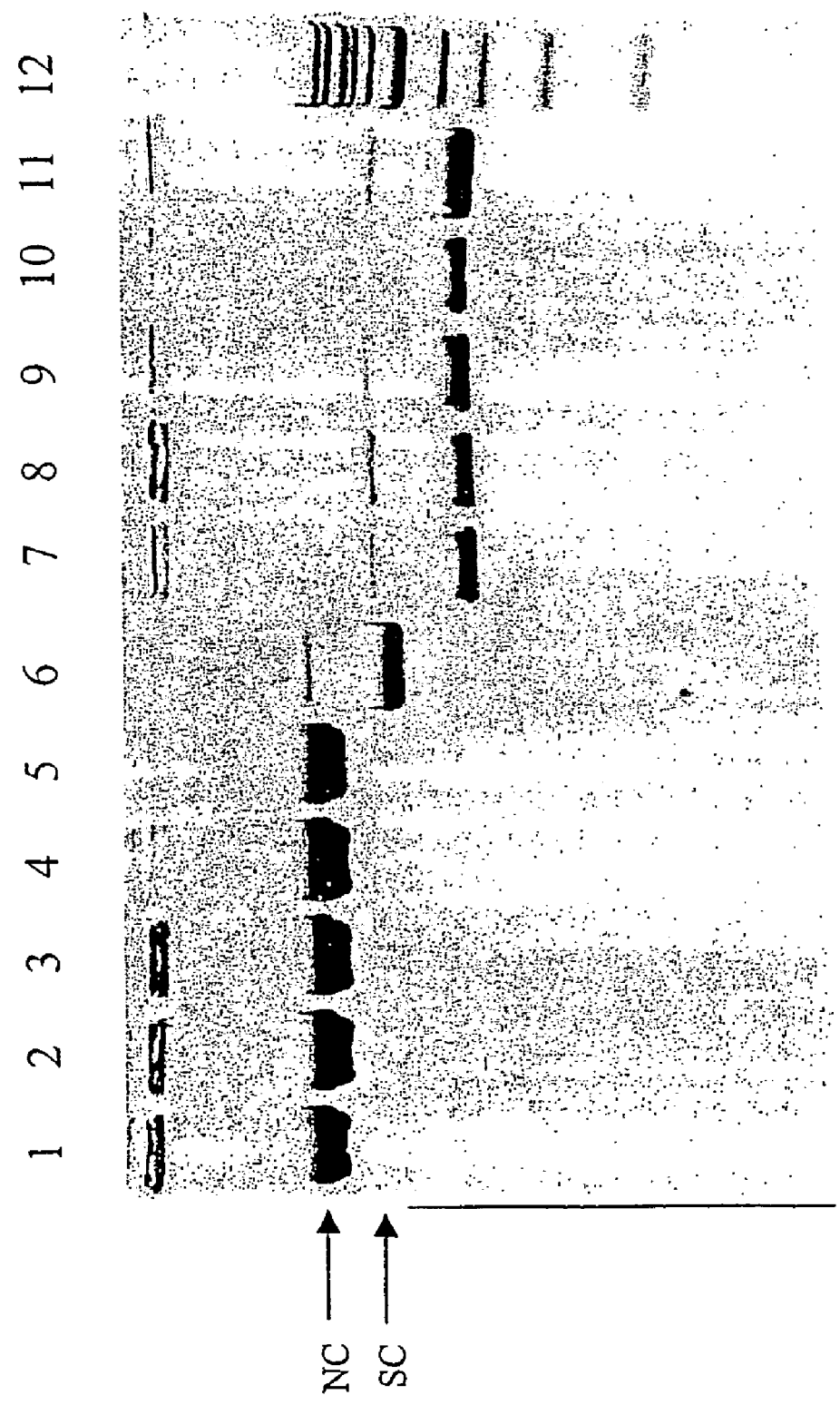
FIG. 2 shows the DNA nicking activity assay for Nb.BsmI (R507D/G509V/E546V) at different temperatures. Lanes 1 to 5, pBR322 digested with Nb.BsmI at 65° C., 70° C., 75° C., 37° C., and 25° C., respectively; lane 6, control-pBR322DNA absent BsmI; lanes 7-10, pUC19 DNA (no site for BsmI) incubated with Nb.BsmI at 70° C., 75° C., 37° C., and 25° C., respectively; lane 11, pUC19 DNA (no BsmI site); lane 12, DNA size marker. NC, nicked circular DNA. SC, supercoiled circular DNA.
Figure 3:
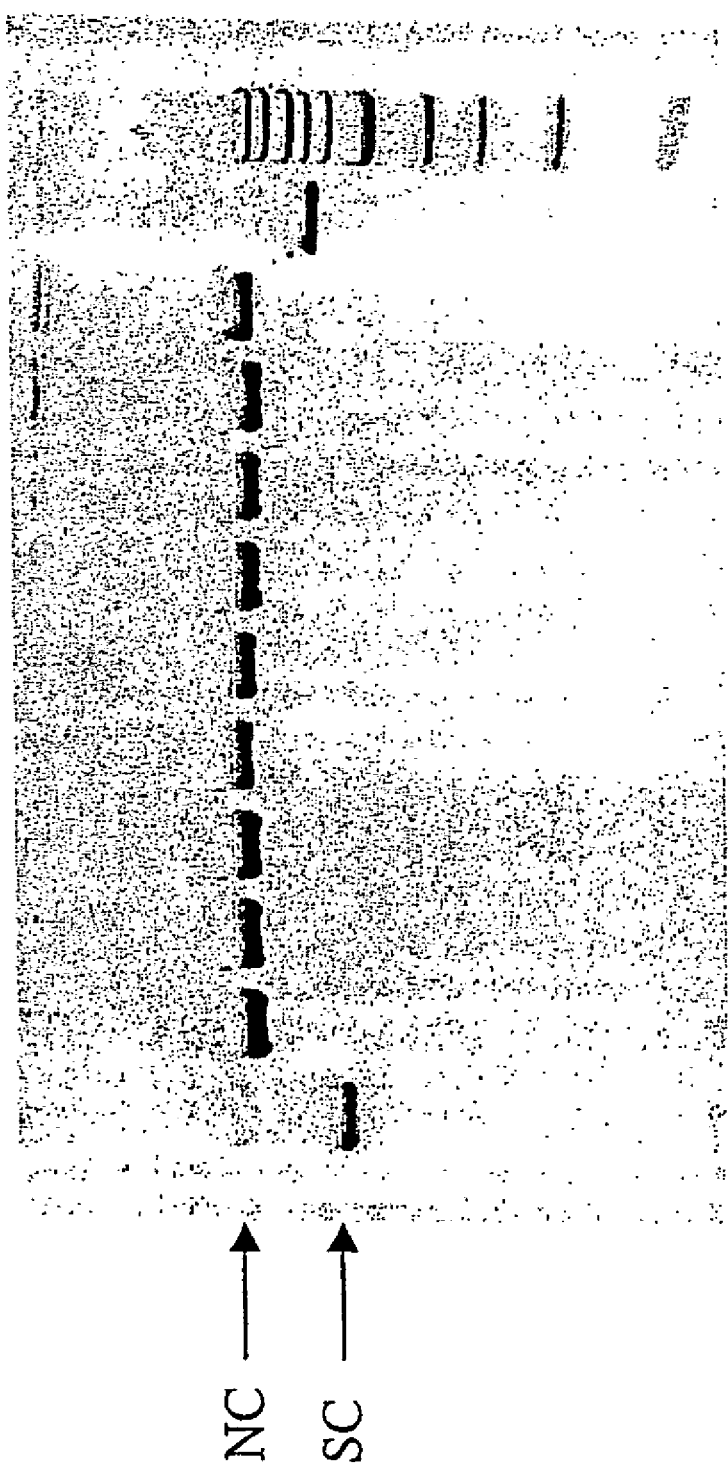
FIG. 3 shows the DNA nicking activity assay for Nb.BsmI (R507D/G509V/E546V) at different enzyme concentration. Lane 1, pBR322; lanes 2 to 10, pBR322 digested with 1, 2, 4, 5, 10, 15, 20, 30, and 40 units of Nb.BsmI, respectively; lane 11, pBR322 linearized with BsmI; lane 12, DNA size marker. NC, nicked circular DNA; SC, supercoiled circular DNA.

In summary, BsmI variant #26 (R507D) displayed high DNA nicking activity and substantially no ds-DNA cleavage activity. Variants R123D, R159D, R364D, R367D, and R526D displayed low to intermediate DNA nicking activity. The rest of the mutants displayed ds-DNA cleavage activity. The most active nicking variant #26 was further characterized. The whole gene was re-sequenced using 6 primers. It was found that in addition to the expected mutation (R507D), there are two additional mutations in the allele. One amino acid substitution (G509V) was introduced by the mutagenic primer. The third mutation/amino acid substitution (E546V) was introduced during inverse PCR. It's known that mutations can be introduced during PCR (the error rate of Deep Vent DNA polymerase is $2 \times 10^{-5}$ per replicated nucleotide). Thus, BsmI nicking variant #26 carried three amino acid substitutions: R507D/G509V/E546V. The DNA nicking activity of Nb.BsmI (R507D/G509V/E546V) is shown in FIGS. 1, 2 and 3.

To investigate the importance of E546V substitution in contributing to the nicking phenotype, the E546V mutation was separated from R507D/G509V by restriction fragment exchange with the wild-type (wt) coding sequence. Cell extract of E546V variant was prepared by sonication and the nicking activity was assayed on pBR322 supercoiled DNA. It was found that the single mutant E546V displayed higher nicking activity than the triple mutant Nb.BsmI (R507D/G509V/E546V), but the ds-DNA cleavage activity is increased somewhat (to about 10%). Fortuitously, when amino acid substitution E546V was combined with R507D substitution (G509V is not likely an important change), the ds-DNA cleavage activity was minimized. It is therefore concluded that some synergistic effect between the two mutations gives rise to the desired nicking endonuclease activity. The nicking variants E546V and R507D/G509V/E546V were partially purified by chromatography through heparin Sepharose and DEAE Sepharose columns and used to nick pBR322 supercoiled DNA. The nicked DNA was gel-purified and used for run-off sequencing. It was determined that nicking variants E546V and R507D/G509V/E546V were bottom-strand nicking enzymes with the specificity of G^CATTC Strandedness was determined by the techniques described in Xu et al. *Journal of Molecular Biology* 337:573-583 (2003)). (^ indicating the nicking position.) The DNA nicking activity of E546V variant is shown in FIG. 4.

Example 3

Purification of Nicking Enzyme Nb.BsmI (R507D/G509V/E546V)

Nb.BsmI (R507D/G509V/E546V) was purified by chromatography through Heparin Hyper-D, Heparin-TSK, Source Q, and Superdex 75 columns or by chromatography through other cation or anion exchange columns or molecular weight sizing column.

Two hundred and sixty grams of frozen cell pellet were resuspended in 780 ml of buffer A (20 mM KPO$_4$ pH 7.1, 0.1 mM EDTA, 10 mM β-mercaptoethanol, 0.2 M NaCl, 5% glycerol). The cells were broken in the Gaulin press and cell debris were removed by high-speed centrifugation. The pH after breakage was 8.0. The assay for determining the nicking activity was done using 322 pBR as the substrate and looking for the supercoiled DNA to be nicked into the relaxed circular form.

1) The first column in the purification was a large Heparin Hyper-D column. This was a capture step. The supernatant was loaded onto the column and a gradient of 0.1 M NaCl to 2.0 M NaCl was applied. The enzyme eluted at about 1.0 M NaCl. The active fractions were pooled and diluted with Standard Buffer, SB (20 mM KPO$_4$ pH 7.1, 0.1 mM EDTA, 10 mM β-mercaptoethanol, 5% glycerol) and salt adjusted to a final concentration of 0.2 M NaCl. This was loaded onto the next column.

2) The second column was a 40 ml Heparin-TSK column. This column concentrated the enzyme. A salt gradient was run using SB/0.2 M NaCl to 2.0 M NaCl. A much sharper peak was obtained and pooled. This was dialyzed against 4 L of SB/0.1 M NaCl. After this purification step, the enzyme was fairly concentrated so a Source-Q was run to eliminate the DNA.

3) A 60 ml Source Q column was loaded with the dialyzed enzyme equilibrated to SB/0.1 M NaCl. As expected, most of the contaminant DNA bound to the Source Q resin. The flow-through was collected and a gradient was run over the Source Q to see if any of the enzyme had bound, but all of the enzyme had come out in the flow-through.

4) The enzyme in the Source Q flow-through (at a NaCl concentration of 0.1 M) was loaded back onto the Heparin TSK column and a sharp gradient was applied up to 2.0 M NaCl. The enzyme was pooled to keep the volume down to 30 ml and loaded onto a molecular weight sizing column.

5) The Superdex 75 was run with 4 L of 20 mM Tris-HCl, pH 7.6, 0.1 mM EDTA, 10 mM b-mercaptoethanol, 0.5 M NaCl, 5% glycerol. Three symmetric peaks were detected in the fraction collector and the middle peak had most of the nicking activity. The fractions in the middle peak were pooled and dialyzed into storage buffer (15 mM Tris-HCl pH 7.2, 0.1 mM EDTA, 1 mM DTT, 0.15 M NaCl, 50% glycerol).

Figure 5:
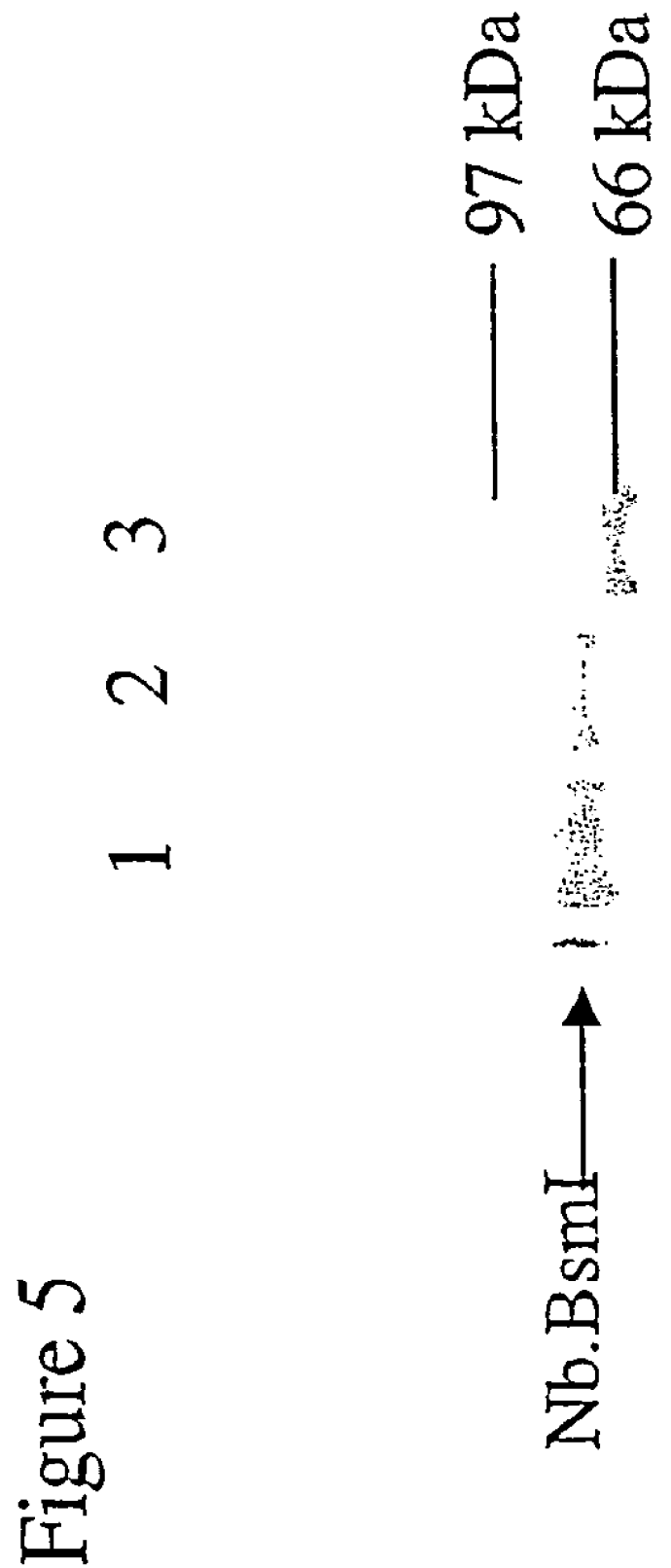
FIG. 5 is an analysis of purified Nb.BsmI (R507D/G509V/E546V) restriction endonuclease on SDS-PAGE. Lanes 1 and 2, purified Nb.BsmI (R507D/G509V/E546V); lane 3, protein size marker.

6) The final enzyme was titered for concentration and subsequent quality controls were done. The purified Nb.BsmI (R507D/G509V/E546V) is shown in FIG. 5.

Example 4

Determination of the Optimal Assay Condition for Nb.BsmI

Enzyme catalytic efficiencies sometimes are greatly influenced by buffer conditions. Therefore, Nb.BsmI nicking activity was assayed in different buffers, such as NEB (New England Biolabs, Inc., Ipswich, Mass.) buffers 1 (no NaCl), 2 (50 mM NaCl), 3 (100 mM NaCl), and 4 (50 mM potassium acetate buffer), BamHI buffer (150 mM NaCl), Thermopol buffer, Taq DNA pol buffer, and some other special restriction buffers such as Sau3AI and MwoI buffers. Nicking assay conditions were 0.5 µg pBR322 substrate, 5 µL 10× buffer, 2 µl Nb.BsmI (~40 units), total volume adjusted to 50 µl with sterile distilled water. Nicking reactions were carried out at 65° C. for 1 h. FIG. 1 shows that the Nb.BsmI is active in all the buffers tested. To minimize the ds-DNA cleavage, the preferred buffers are buffer 3 and BamHI buffer (100 to 150 mM NaCl). The Nb.BsmI nicking enzyme is also active in Thermopol buffer and Taq DNA pol buffer and therefore should be compatible with thermostable DNA polymerases such as Bst, Taq, Vent, and Deep Vent DNA polymerases.

The nicking assays were also performed at temperatures ranging from 25° C. to 75° C. in NEB buffer 3 (100 mM NaCl) (New England Biolabs, Inc., Ipswich, Mass.). FIG. 2 shows that Nb.BsmI is active in the wide range of temperatures. It is active at 25° C. to 75° C. in the nicking reactions.

In the DNA nicking reactions, it is desirable to minimize the ds-DNA cleavage. Therefore, 4- to 80-fold over-digestions were performed on pBR322 in order to detect nicked circular DNA and/or linear DNA. The following assay condition was used: 0.5 µg pBR322 substrate, 5 µl 10× buffer 3, 1-5 µl diluted and undiluted Nb.BsmI (1 to 40 units), adjusted volume to 50 µl with sterile distilled water. Nicking reactions were carried out at 65° C. for 1 h. FIG. 3 shows that 40 units of Nb.BsmI generated a weak linear band (at ~80-fold over-digestion). No linear DNA was detected with 1 to 30 units of Nb.BsmI digestion. It was concluded that no more than 60-fold over-digestion should be carried out in order to minimize ds-DNA cleavage.

Example 5

Glutamic Acid Mutagenesis Scanning of BsmI Endonuclease to Isolate Nicking Variants The E546V substitution was introduced during inverse PCR amplification, which resulted in a nicking phenotype. Site-directed mutagenesis can change each Asp residue to a non-charged hydrophobic residue such as Val, Met, Ile, Leu, or any other amino acid residues other than Asp and Glu. Cell extracts can be prepared from the mutant cell cultures and assayed for DNA nicking activity on appropriate DNA substrates. The nicking strand specificity can be determined by run-off sequencing.

Alternatively, the Asn, Gln, and Lys residues in BsmI restriction endonuclease can be mutated to generate nicking variants either by site-directed mutagenesis, localized random mutagenesis or random mutagenesis. The nicking variants can be purified by cation or anion exchange columns or molecular weight sizing column. BsmI nicking variants can also be purified by heat denaturation. *E. coli* host proteins can be heat-denatured by heating the cell extracts at 50° C. to 75° C. for 20 to 60 min. Heat-denatured proteins can be removed by high speed centrifugation. The supernatant contains the partially purified nicking enzyme.

The invention claimed is:

1. An isolated, purified or recombinant nicking endonuclease comprising an amino acid sequence that can be encoded by a DNA at least 90% identical to SEQ ID NO:5, wherein said amino acid sequence does not have an arginine residue at a position corresponding to position 507 in SEQ ID NO:6 and does not have a glutamic acid residue at a position corresponding to position 546 in SEQ ID NO:6.

2. A nicking endonuclease according to claim 1, wherein the amino acid sequence has an aspartic acid residue at a position corresponding to position 507 of SEQ ID NO:6 and a valine residue at a position corresponding to position 546 of SEQ ID NO:6.

* * * * *

SEQUENCE LISTING

<160> NUMBER OF SEQ ID NOS: 6

<210> SEQ ID NO 1
<211> LENGTH: 54
<212> TYPE: DNA
<213> ORGANISM: unknown

-continued

```
<220> FEATURE:
<223> OTHER INFORMATION: primer

<400> SEQUENCE: 1
ggtggtgcat gcggaggtaa ataaatgaat gtttttagaa ttcatggtga taat         54

<210> SEQ ID NO 2
<211> LENGTH: 39
<212> TYPE: DNA
<213> ORGANISM: unknown
<220> FEATURE:
<223> OTHER INFORMATION: primer

<400> SEQUENCE: 2
ggtggtgacg tcttatccct ctatatgaaa aaatcctgt                           39

<210> SEQ ID NO 3
<211> LENGTH: 39
<212> TYPE: DNA
<213> ORGANISM: unknown
<220> FEATURE:
<223> OTHER INFORMATION: primer

<400> SEQUENCE: 3
agcggcctat caataataga taatggtcat ggatttagg                           39

<210> SEQ ID NO 4
<211> LENGTH: 39
<212> TYPE: DNA
<213> ORGANISM: unknown
<220> FEATURE:
<223> OTHER INFORMATION: primer

<400> SEQUENCE: 4
cctaaattca tgaacattat ctattattga taggccact                           39

<210> SEQ ID NO 5
<211> LENGTH: 2031
<212> TYPE: DNA
<213> ORGANISM: unknown
<220> FEATURE:
<223> OTHER INFORMATION: bacillus stearothermophilus NUB36

<400> SEQUENCE: 5
atgaatgttt ttagaattca tggtgataat attattgagt gtgagagagt tatagatttg    60
atattatcaa aaatcaatcc ccagaaagta aaaagagggt ttatttcatt atcatgccct   120
tttatagaaa ttatattcaa agagggtcat gattattttc actggcgttt tgatatgttt   180
cctggattca ataaaaatac taacgacaga tggaatagca atattttaga tttgttaagt   240
caaaaaggaa gttttttgta tgaaactcca gatgtaataa ttaccagttt aaataatgga   300
aaagaagaaa ttttaatggc gatagaattt tgtagtgctt tacaagcagg taaccaagct   360
tggcaaagaa gtgggcgagc atattcggta ggtcgaacag ggtacccata tatatacata   420
gtagattttg ttaaatacga gttgaataat agtgatagat ctagaaaaaa cttgagattc   480
ccaaatccag ctataccata tagttacata agtcactcaa aaaacactgg taattttatt   540
gtgcaagcat attttagagg agaagaatat cagccaaagt atgataaaaa acttaaattt   600
tttgatgaaa ctatatttgc agaagatgac attgcagact atataattgc aaagctacag   660
catcgcgata ccagcaatat agaacaatta ttgataaaca aaaacttaaa aatggttgaa   720
ttcttatcaa aaaatacaaa aaatgataat aacttcacat attcagaatg ggagagtatc   780
tacaatggta catatagaat aacaaattta cctagtttag ggagatttaa atttaggaaa   840
```

```
aagattgctg aaaagtctct ttcaggaaaa gttaaggaat ttaacaatat tgttcagaga    900
tatagtgtag gtcttgcttc aagtgattta cctttggag ttataagaaa agaatcaaga    960
aatgatttta ttaacgatgt atgtaaactt tataatataa atgatatgaa ataattaaa   1020 gagctaaaag aagatgcgga ccttattgtc tgtatgctta agggatttaa acctagagga  1080
gatgataatc gaccggatag aggagcgtta ccccttgttg ctatgctagc cggagaaaat  1140
gcacaaattt ttacatttat ttatggacca ttaataaaag gggctataaa tttgattgac  1200
caggatatca ataagcttgc aaaacgtaac gggctttgga aatcctttgt aagtttaagt  1260
gactttattg ttttggactg tcctattatc ggagaatctt ataatgaatt tcgtttaatc  1320
ataaataaga acaataaaga gtccatttta cgcaaaacta gcaaacaaca aaatatttttg 1380 gttgatccaa cacctaatca ttatcaagaa atgatgtgg atacagttat atactctata  1440
tttaaatata ttgtacctaa ttgttttagt gggatgtgta atccacctgg aggagactgg 1500
agtggcctat caataataag aaatggtcat gaatttaggt ggttatcact tcctcgagtt  1560
agtgagaatg gaaaaagacc cgaccatgta atacaaatac ttgatctttt tgaaaaaccc  1620
cttttattaa gtattgagtc aaaagaaaaa cctaatgatc ttgaaccaaa ataggggtg   1680 cagttaataa aatacataga gtatctatttt gattttactc ctagtgttca agaaagata   1740 gccgggggaa attgggagtt tggtaataaa agcctggttc ctaacgattt tattctattg  1800
tctgcaggtg cattcatcga ttatgacaat cttacagaaa atgattatga aaaattttt   1860 gaagtcactg gttgtgattt actgattgct attaaaaacc agaataaccc tcagaagtgg  1920
gtgattaaat tcaaacctaa aaatactata gcagagaaat tagttaacta tataaagctt  1980
aattttaaaa gtaatatatt tgatacagga ttttttcata tagagggata a           2031
```

<210> SEQ ID NO 6
<211> LENGTH: 676
<212> TYPE: PRT
<213> ORGANISM: unknown
<220> FEATURE:
<223> OTHER INFORMATION: bacillus stearothermophilus NUB36

<400> SEQUENCE: 6

```
Met Asn Val Phe Arg Ile His Gly Asp Asn Ile Ile Glu Cys Glu Arg
1               5                   10                  15

Val Ile Asp Leu Ile Leu Ser Lys Ile Asn Pro Gln Lys Val Lys Arg
            20                  25                  30

Gly Phe Ile Ser Leu Ser Cys Pro Phe Ile Glu Ile Phe Lys Glu
        35                  40                  45

Gly His Asp Tyr Phe His Trp Arg Phe Asp Met Phe Pro Gly Phe Asn
    50                  55                  60

Lys Asn Thr Asn Asp Arg Trp Asn Ser Asn Ile Leu Asp Leu Leu Ser
65                  70                  75                  80

Gln Lys Gly Ser Phe Leu Tyr Glu Thr Pro Asp Val Ile Ile Thr Ser
                85                  90                  95

Leu Asn Asn Gly Lys Glu Glu Ile Leu Met Ala Ile Glu Phe Cys Ser
            100                 105                 110

Ala Leu Gln Ala Gly Asn Gln Ala Trp Gln Arg Ser Gly Arg Ala Tyr
        115                 120                 125

Ser Val Gly Arg Thr Gly Tyr Pro Tyr Ile Tyr Ile Val Asp Phe Val
    130                 135                 140

Lys Tyr Glu Leu Asn Asn Ser Asp Arg Ser Arg Lys Asn Leu Arg Phe
145                 150                 155                 160
```

```
Pro Asn Pro Ala Ile Pro Tyr Ser Tyr Ile Ser His Ser Lys Asn Thr
                165                 170                 175

Gly Asn Phe Ile Val Gln Ala Tyr Phe Arg Gly Glu Tyr Gln Pro
        180                 185                 190

Lys Tyr Asp Lys Leu Lys Phe Phe Asp Glu Thr Ile Phe Ala Glu
            195                 200                 205

Asp Asp Ile Ala Asp Tyr Ile Ile Ala Lys Leu Gln His Arg Asp Thr
210                 215                 220

Ser Asn Ile Glu Gln Leu Leu Ile Asn Lys Asn Leu Lys Met Val Glu
225                 230                 235                 240

Phe Leu Ser Lys Asn Thr Lys Asn Asp Asn Asn Phe Thr Tyr Ser Glu
                245                 250                 255

Trp Glu Ser Ile Tyr Asn Gly Thr Tyr Arg Ile Thr Asn Leu Pro Ser
                260                 265                 270

Leu Gly Arg Phe Lys Phe Arg Lys Ile Ala Glu Lys Ser Leu Ser
            275                 280                 285

Gly Lys Val Lys Glu Phe Asn Asn Ile Val Gln Arg Tyr Ser Val Gly
290                 295                 300

Leu Ala Ser Ser Asp Leu Pro Phe Gly Val Ile Arg Lys Glu Ser Arg
305                 310                 315                 320

Asn Asp Phe Ile Asn Asp Val Cys Lys Leu Tyr Asn Ile Asn Asp Met
                325                 330                 335

Lys Ile Ile Lys Glu Leu Lys Glu Asp Ala Asp Leu Ile Val Cys Met
                340                 345                 350

Leu Lys Gly Phe Lys Pro Arg Gly Asp Asp Asn Arg Pro Asp Arg Gly
                355                 360                 365

Ala Leu Pro Leu Val Ala Met Leu Ala Gly Glu Asn Ala Gln Ile Phe
                370                 375                 380

Thr Phe Ile Tyr Gly Pro Leu Ile Lys Gly Ala Ile Asn Leu Ile Asp
385                 390                 395                 400

Gln Asp Ile Asn Lys Leu Ala Lys Arg Asn Gly Leu Trp Lys Ser Phe
                405                 410                 415

Val Ser Leu Ser Asp Phe Ile Val Leu Asp Cys Pro Ile Ile Gly Glu
                420                 425                 430

Ser Tyr Asn Glu Phe Arg Leu Ile Ile Asn Lys Asn Asn Lys Glu Ser
                435                 440                 445

Ile Leu Arg Lys Thr Ser Lys Gln Gln Asn Ile Leu Val Asp Pro Thr
                450                 455                 460

Pro Asn His Tyr Gln Glu Asn Asp Val Asp Thr Val Ile Tyr Ser Ile
465                 470                 475                 480

Phe Lys Tyr Ile Val Pro Asn Cys Phe Ser Gly Met Cys Asn Pro Pro
                485                 490                 495

Gly Gly Asp Trp Ser Gly Leu Ser Ile Ile Arg Asn Gly His Glu Phe
                500                 505                 510

Arg Trp Leu Ser Leu Pro Arg Val Ser Glu Asn Gly Lys Arg Pro Asp
                515                 520                 525

His Val Ile Gln Ile Leu Asp Leu Phe Glu Lys Pro Leu Leu Leu Ser
                530                 535                 540

Ile Glu Ser Lys Glu Lys Pro Asn Asp Leu Pro Lys Ile Gly Val
545                 550                 555                 560

Gln Leu Ile Lys Tyr Ile Glu Tyr Leu Phe Asp Phe Thr Pro Ser Val
                565                 570                 575

Gln Arg Lys Ile Ala Gly Gly Asn Trp Glu Phe Gly Asn Lys Ser Leu
```

-continued

```
                        580                     585                     590
Val Pro Asn Asp Phe Ile Leu Leu Ser Ala Gly Ala Phe Ile Asp Tyr
        595                     600                     605

Asp Asn Leu Thr Glu Asn Asp Tyr Glu Lys Ile Phe Glu Val Thr Gly
        610                     615                     620

Cys Asp Leu Leu Ile Ala Ile Lys Asn Gln Asn Asn Pro Gln Lys Trp
625                     630                     635                     640

Val Ile Lys Phe Lys Pro Lys Asn Thr Ile Ala Glu Lys Leu Val Asn
                645                     650                     655

Tyr Ile Lys Leu Asn Phe Lys Ser Asn Ile Phe Asp Thr Gly Phe Phe
                660                     665                     670

His Ile Glu Gly
        675
```